(12) United States Patent
Morrissey et al.

(10) Patent No.: US 11,519,917 B2
(45) Date of Patent: Dec. 6, 2022

(54) ASSAY FOR QUANTIFYING POLYPHOSPHATES

(71) Applicants: THE REGENTS OF THE UNIVERSITY OF MICHIGAN, Ann Arbor, MI (US); THE BOARD OF TRUSTEES OF THE UNIVERSITY OF ILLINOIS, Urbana, IL (US)

(72) Inventors: James H. Morrissey, Ann Arbor, MI (US); Stephanie A. Smith, Ann Arbor, MI (US); Catherine J. Baker, Ann Arbor, MI (US); Rachel Hemp, Ann Arbor, MI (US); Richard J. Travers, Ann Arbor, MI (US)

(73) Assignees: THE REGENTS OF THE UNIVERSITY OF MICHIGAN, Ann Arbor (ML); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 648 days.

(21) Appl. No.: 16/604,269

(22) PCT Filed: Apr. 13, 2018

(86) PCT No.: PCT/US2018/027425
§ 371 (c)(1),
(2) Date: Oct. 10, 2019

(87) PCT Pub. No.: WO2018/191582
PCT Pub. Date: Oct. 18, 2018

(65) Prior Publication Data
US 2020/0150126 A1 May 14, 2020

Related U.S. Application Data

(60) Provisional application No. 62/485,380, filed on Apr. 13, 2017.

(51) Int. Cl.
*G01N 33/58* (2006.01)
*C01B 25/37* (2006.01)
(Continued)

(52) U.S. Cl.
CPC ............ *G01N 33/58* (2013.01); *C01B 25/37* (2013.01); *C01B 25/40* (2013.01); *G01N 33/86* (2013.01);
(Continued)

(58) Field of Classification Search
CPC .. G01N 33/58; G01N 33/86; G01N 2333/245; G01N 2333/7454;
(Continued)

(56) References Cited

U.S. PATENT DOCUMENTS

2003/0073830 A1 4/2003 Heath et al.
2003/0162213 A1 8/2003 Fuller et al.
(Continued)

FOREIGN PATENT DOCUMENTS

EP 1402024 B1 8/2007
WO WO20140072545 3/2014

OTHER PUBLICATIONS

Barua et al. Discovery of cationic polymers for non-viral gene delivery using combinatorial approaches. Comb Chem High Throughput Screen. Dec. 2011;14(10):908-24.
(Continued)

*Primary Examiner* — Jennifer Wecker
*Assistant Examiner* — Michael Paul Shimek
(74) *Attorney, Agent, or Firm* — Casimir Jones, S.C.; Tanya A. Arenson (57) ABSTRACT

Provided herein are compositions and methods for quantifying polyphosphates. In particular, provided herein are
(Continued)

solution and substrate based assays for quantifying polyphosphates in complex samples.

19 Claims, 8 Drawing Sheets (51) Int. Cl.
*C01B 25/40* (2006.01)
*G01N 33/86* (2006.01)
(52) U.S. Cl.
CPC ............... *G01N 2333/245* (2013.01); *G01N 2333/7454* (2013.01); *G01N 2333/96444* (2013.01)
(58) Field of Classification Search
CPC .......... G01N 2333/96444; G01N 33/84; C01B 25/37; C01B 25/40; C01B 25/38
See application file for complete search history.

(56) References Cited

U.S. PATENT DOCUMENTS

2006/0198837 A1 9/2006 Morrissey et al.
2014/0227712 A1 8/2014 Horlitz et al.
2014/0303084 A1 10/2014 Thorn et al.
2016/0060687 A1 3/2016 Zhu et al.

OTHER PUBLICATIONS

Choi et al. Phosphoramidate end labeling of inorganic polyphosphates: facile manipulation of polyphosphate for investigating and modulating its biological activities. Biochemistry. Nov. 16, 2010;49(45):9935-41.

Diaz et al. Fluorometric quantification of natural inorganic polyphosphate. Environ Sci Technol. Jun. 15, 2010;44(12):4665-71.

International Search Report and Written Opinion for PCT/US2018/027425, dated Jul. 16, 2018, 11 pages.

Saito et al. Direct labeling of polyphosphate at the ultrastructural level in *Saccharomyces cerevisiae* by using the affinity of the polyphosphate binding domain of *Escherichia coli* exopolyphosphatase. Appl Environ Microbiol. Oct. 2005;71(10):5692-701.

Santi et al. Novel assay for prothrombotic polyphosphates in plasma reveals their correlation with obesity. Thromb Res. Aug. 2016;144:53-5.

Schlagenhauf et al. Non-enzymatic quantification of polyphosphate levels in platelet lysates and releasates. J Pharm Biomed Anal. Nov. 30, 2016;131:1-5.

Shenoi et al. Affinity-based design of a synthetic universal reversal agent for heparin anticoagulants.Sci Transl Med. Oct. 29, 2014;6(260):260ra150.

FIG. 1
ASSAY STRUCTURE

VERSION B

FIG. 8

ASSAY FOR QUANTIFYING POLYPHOSPHATES

CROSS-REFERENCE TO RELATED APPLICATIONS

This application is a 371 U.S. National Phase Entry of pending International Application No. PCT/US2018/027425, filed Apr. 13, 2018, which claims priority to Provisional Patent Application 62/485,380, filed Apr. 13, 2017, which are herein incorporated by reference in their entireties.

STATEMENT REGARDING FEDERALLY SPONSORED RESEARCH OR DEVELOPMENT

This invention was made with government support under contract numbers R01 HL047014, UM1HL120877, and R35 HL135823 awarded by the National Institutes of Health. The government has certain rights in the invention.

FIELD

Provided herein are compositions and methods for quantifying polyphosphates. In particular, provided herein are solution and substrate based assays for quantifying polyphosphates in complex samples.

BACKGROUND

Inorganic polyphosphate (polyP) is a potent procoagulant molecule, affecting multiple steps in the clotting cascade. PolyP is also proinflammatory and regulates the complement cascade. PolyP released from platelets, inflammatory cells, and/or infectious organisms may be important in the pathophysiology of many procoagulant and inflammatory diseases, including sepsis and trauma. Consequently, it is desirable to quantify polyP in plasma. Unfortunately, the currently available methods capable of quantifying polyP in complex biological samples such as plasma, serum, cell lysates, sewage sludge or wastewater are difficult and extremely laborious, severely limiting their use in clinical studies.

Previous methods used to extract polyP from biological fluids are laborious and difficult. They include repeated phenol/chloroform extraction, use of anion exchanger resin, and silica filter or glass milk based purification protocols. A publication described use of silica columns to purify polyP from cell extracts, followed by detection with DAPI (Schlagenhauf A, et al., J Pharm Biomed Anal. 2016 Nov. 30; 131:1-5). A separate publication described the use of DAPI for directly quantifying polyP in wastewater (Diaz J M, et al., Environ Sci Technol. 2010 Jun. 15; 44(12):4665-71).

The laboratory of Felix Ruiz at the University of Cadiz, Spain has described a method that involves the cryoprecipitation of plasma proteins and polyP from plasma samples, followed by the exopolyphosphatase-mediated digestion of the attached polyP and subsequent quantification of the released monophosphate (Santi M J, et al., Thromb Res. 2016 August; 144:53-5).

Additional methods to detect and quantify polyphosphates in samples, especially complex samples, are needed.

SUMMARY

Provided herein are compositions and methods for quantifying polyphosphates. In particular, provided herein are solution and substrate based assays for quantifying polyphosphates in complex samples.

As research and understanding of the physiological effects of polyP continues to grow, so does the need to study it in clinical samples. With the assays described herein, effective concentrations of polyP in plasma or other complex samples are determined utilizing widely available equipment. Furthermore, the assays described herein are capable of detecting polyP of the size range secreted by activated human platelets (e.g., approximately 60 to 100 phosphates in length), as well as longer polymers found in other samples. Evaluating polyP concentrations from patients with different disease conditions leads to improved understanding of the physiological roles of polyP in disease, and aids in determining therapeutic strategy and prognosis.

For example, in some embodiments, provided herein is a method of detecting polyphosphate in a sample, comprising: a) contacting a sample comprising polyphosphate with an agent that inhibits binding of the polyphosphate to proteins and other substances in the sample; b) contacting the sample with a solid support (e.g., sample well) coated in a polymer under conditions such that the polyphosphate binds to the polymer; c) washing the solid support (e.g., sample well) to aid in removal of proteins and other competing polyphosphate-binding substances in the sample; and d) detecting the level of polyP bound to the polymer. In some embodiments, step d) comprises contacting the sample well with a polyphosphate-binding protein or other entity (e.g., the isolated, recombinant polyP-binding domain of E. coli exopolyphosphatase (PPXbd) Saito et al. Appl Environ Microbiol. 2005; 71(10):5692-5701) under conditions such that the polyphosphate binding entity binds to polyphosphate (e.g., in the sample well); and quantifying the level of polyphosphate binding protein bound to the polyphosphate. In some embodiments, the polyphosphate binding protein is labeled (e.g., with biotin (biotPPXbd)). In some embodiments, the quantifying is chemical quantification (e.g., by completely hydrolyzing the polyP to monophosphate units, and then quantifying the amount of released monophosphate).

Further embodiments provide a method of detecting polyphosphate in a sample, comprising: a) contacting a sample comprising polyphosphate with an agent that inhibits binding of the polyphosphate to proteins in the sample and a known amount of labeled (e.g., biotin labelled) polyphosphate; b) contacting the sample with a solid support (e.g., sample well) coated in a polymer under conditions such that the polyphosphate binds to said polymer; c) washing the solid support (e.g., sample well) to remove proteins and other competing polyP-binding substances in the sample; and d) quantifying the level of labeled polyphosphate one the solid support (e.g., in the sample well).

In some embodiments, the polymer is polyethylenimine. In some embodiments, the agent that inhibits binding is a salt (e.g., LiCl) and/or a denaturing agent (e.g., SDS, urea, guanidine HCl, guanidine isothiocyanate, or sodium thiocyanate). The present disclosure is not limited to any particular type of sold support. Examples include, but are not limited to, sample wells, beads, columns, resins, plates, etc. In some embodiments, the solid support is a sample well. The present disclosure is not limited to particular sample well configurations. In some embodiments, the sample well is a well of a microtiter plate or other substrate. In some embodiments, the quantifying comprises contacting said sample with streptavidin-peroxidase and a substrate for said peroxidase. In some embodiments, washing the sample comprises washing with a buffer comprising urea and a salt and/or a denaturing agent (e.g., to further denature polyP-binding proteins and assist with their removal). In some embodiments, the quantifying comprising comparing the amount of substrate to a standard curve. In some embodiments, the sample is a biological sample or an environmental sample. In some embodiments, the environmental sample is a water sample. Exemplary biological samples include, but are not limited to, blood, plasma, serum, cerebrospinal fluid, lavage fluid, or stool. In some embodiments, the polyphosphate is 20 to 5000 units (e.g., 50 to 100, 60 to 100, 20 to 1000, 40 to 500, 50 to 1000, 50 to 500, 60 to 1000, or 60 to 500 units) in length. In some embodiments, the sample is from a human subject diagnosed with or suspected of having a disease or condition selected from, for example, deep vein thrombosis, sepsis, trauma, cancer, a clotting disorder, an inflammatory disease, or a fibrotic disease.

Additional embodiments provide a kit or system, comprising: a) a solid support (e.g., a sample well) coated with a polymer (e.g., polyethylenimine); and b) a solution comprising an agent that inhibits binding of polyphosphates to proteins (e.g., a salt). In some embodiments, the kit or system further comprises labeled polyphosphate. In some embodiments, the kit or system further comprises one or more additional components selected from, for example, a wash buffer comprising urea and a salt; a streptavidin-peroxidase complex, or a chromogenic substrate for the peroxidase.

Yet other embodiments provide a method of detecting polyphosphate in a sample, comprising: a) contacting a plurality of plasma samples comprising polyphosphate with a reagent that triggers clotting (e.g., tissue factor) and a variety of concentrations of tissue factor pathway inhibitor; and b) measuring the clotting time of the sample. In some embodiments, the clotting time is related to the level of polyphosphate in the sample. In some embodiments, the reagent comprises tissue factor, phospholipid vesicles, and a buffer. In some embodiments, step a) further comprises contacting the sample with $CaCl_2$.

Still other embodiments provide a kit or system, comprising: a) a first reagent comprising tissue factor; and b) a second reagent comprising a tissue factor pathway inhibitor. In some embodiments, the first reagent comprises tissue factor, phospholipid vesicles, and a buffer.

Additional embodiments are described herein.

DEFINITIONS

To facilitate an understanding of the present disclosure, a number of terms and phrases are defined below:

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like, stool, cerebrospinal fluid, lavage fluid, etc. Environmental samples include environmental material such as surface matter, soil, water, and industrial samples. Such examples are not however to be construed as limiting the sample types applicable to the present disclosure.

DETAILED DESCRIPTION

One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

Provided herein are compositions and methods for quantifying polyphosphates. In particular, provided herein are solution and substrate based assays for quantifying polyphosphates in complex samples.

In one embodiment, provided herein is a substrate-based assay that allows for identification and quantification of polyP in liquid biological samples such as plasma or serum or other complex sample types. In one embodiment, the assay allows for a better depiction of the contributions of polyP to various pathological conditions. The assays described herein allow for quantification of polyP in plasma (or serum) samples as a descriptor of severity of disease, quantification of propensity for hypercoagulability, and prognostication.

In some embodiments, provided herein is a high-throughput assay (e.g., microplate assay) that is adaptable to both the research laboratory setting, for automated hematology analyzer systems currently in use in clinical diagnostic laboratories, and as point-of-care test systems.

In some embodiments, solid support based assays (e.g., sample wells of a microtiter plate or other substrate or solid support) are used in quantify polyP. In some embodiments, sample wells are coated with a polymer that binds to polyP (e.g., in the presence of a salt of high ionic strength). In some embodiments, the initial sample and/or wash buffer further comprise a denaturing agent (e.g., urea, guanidine HCl, guanidine isothiocyanate, or sodium thiocyanate).

Figure 1:
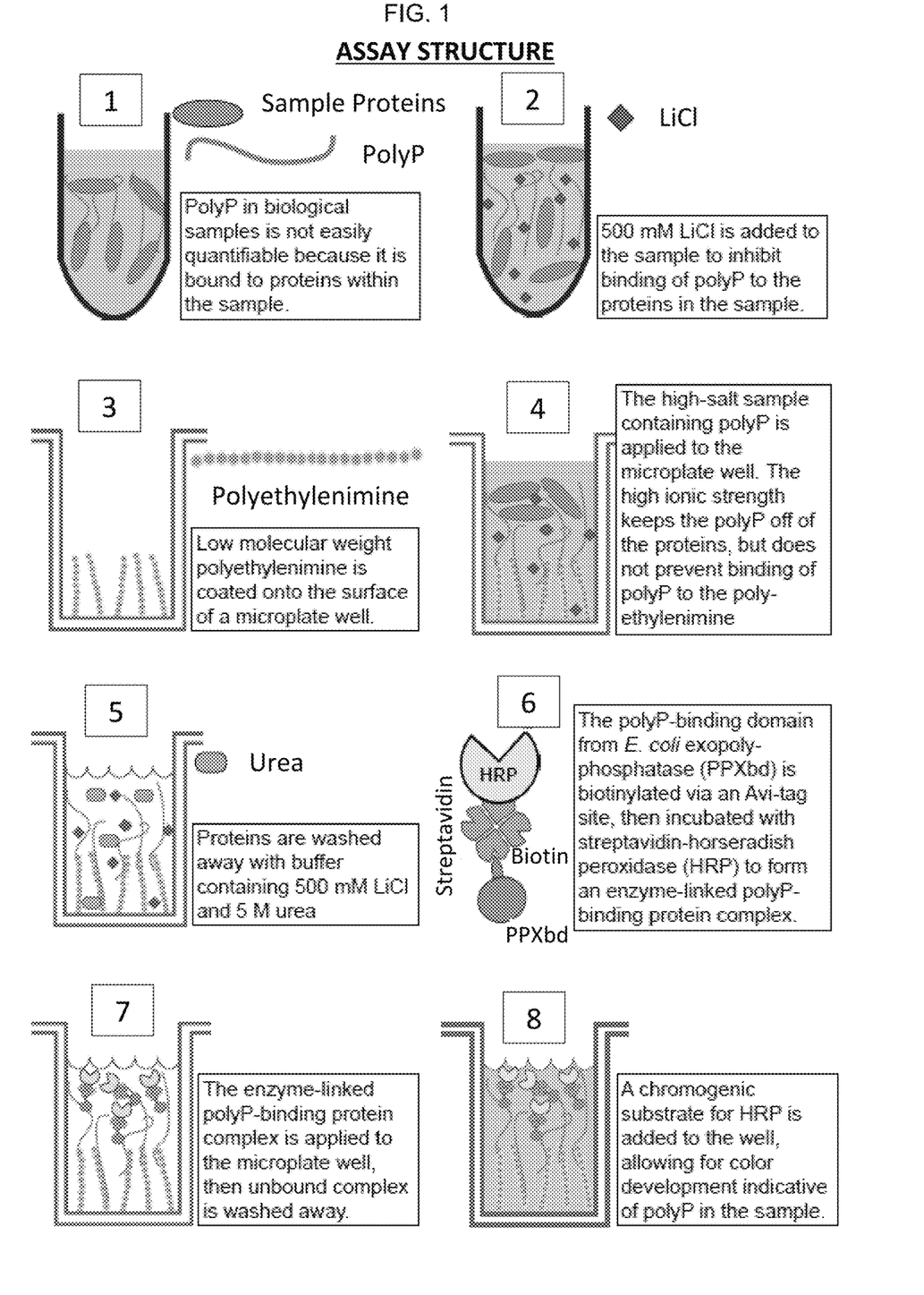
FIG. 1 shows an exemplary assay configuration.

Example 1 describes exemplary, non-limiting examples of substrate-based assays for detection and quantification of polyP (See e.g., FIG. 1). In some embodiments, the substrate-based assay allows for the detection and quantification of polyP in the presence of large amounts of polyP-binding proteins and other polyP-binding substances like polyamines such as are present in biological or environmental samples. In some embodiments, this assay leverages the high binding affinity of polyP for the cationic polymer, polyethylenimine (PE). The polyP/PE interaction is resistant to high ionic strength, whereas most proteins will no longer bind polyP under these conditions. In some embodiments, samples (e.g., biological or environmental samples) are incubated with a PE-coated surface. The sample wells are then washed to remove unbound proteins from the immobilized polyP. The captured polyP is then detected using a polyP binding protein (e.g., recombinant bacterial polyP-binding protein) or chemically quantified. In some embodiments, the polyP binding protein is labeled (e.g., with biotin). In some embodiments, the amount of bound polyP is then quantified using a streptavidin-peroxidase system comprising a chromogenic, fluorogenic or chemiluminescent substrate. In some embodiments, the quantifying is chemical quantification (e.g., comprising hydrolyzing the polyP to monophosphate units, and then quantifying the amount of released monophosphate using a chemical or enzymatic method). An exemplary chemical method for hydrolyzing the bound polyP is heating to 100° C. in the presence of 1 N HCl. An exemplary enzymatic method for hydrolyzing the bound polyP is digestion at 37° C. with 5 units/mL calf intestinal alkaline phosphatase in 50 mM Tris-HCl pH 7.4, 1 mM $MgCl_2$, and 0.1 mM $ZnCl_2$. An exemplary chemical method for quantifying the released monophosphate is the malachite green phosphate assay (Choi et al. Biochemistry 49:9935-9941, 2010). An exemplary enzymatic method for quantifying the released monophosphate is the PiPer™ Phosphate Assay Kit (ThermoFisher Scientific).

The present disclosure is not limited to a particular polymer. In some embodiments, the polymer is polyethylenimine (PE). In some embodiments, the polymer comprises a high density of positive charges and a suitable polymer size (e.g., a suitable number and density of positive charges) such that the polymer binds polyP tightly via electrostatic interactions. The capture matrix need not necessarily even be a polymer, as long as the capture material has a high concentration of positive charges and can be immobilized onto multiplate wells, or attached to beads or another suitable surface or matrix for the assay.

Additional examples of cationic polymers include, but are not limited to, cationic polypeptides like polylysine, polyornithine and polyarginine, linear or branched synthetic, cationic polymers like polybrene, and cationic polymers under investigation for non-viral gene delivery (e.g., since polyP and nucleic acids both have repeating, anionic phosphate groups and therefore bind to most of the same cationic substances). Examples from Barua et al. (Comb Chem High Throughput Screen. 2011 December; 14(10): 908-924) include, but are not limited to, poly-β-amino esters (PBAEs), branched poly(amino ester) (PAEs), polymethacrylates containing positively charged groups (one example is: poly(2-(dimethylamino)ethyl methacrylate); p(DMAEMA)). In some embodiments, the cationic polymer is polysaccharide-based delivery molecules (e.g., chitosan (a naturally occurring cationic polysaccharide) and cyclodextrin derivatives), polyamine polymers, cationic dendrimers, including Polyamidoamine (PAMAM) dendrimers, and dendrimer-like cationic compounds, including Universal Heparin Reversal Agents (UHRAs); see Shenoi et al. Sci Transl Med. 2014 Oct. 29; 6(260):260ra150).

In some embodiments, the salt is LiCl, although other salts may be utilized. In one exemplary embodiment, the salt is LiCl. In some embodiments, the salt is at high ionic strength. Some additional examples of salts include, but are not limited to, NaCl, KCl, NaI, KI, LiI, guanidine HCl, guanidine isothiocyanate, and sodium thiocyanate. In some embodiments, the avoid precipitation of polyP, the salt does not comprise a divalent metal ion.

The present disclosure is not limited to particular solid supports, labels, detection systems, or detection methods. Exemplary solid supports include, but are not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers.

In some embodiments, the solid support is a planar surface or a particle, such as a bead or microsphere. The bead can be a polystyrene, brominated polystyrene, polyacrylic acid, polyacrylonitrile, polyacrylamide, polyacrolein, polydimethylsiloxane, polybutadiene, polyisoprene, polyurethane, polyvinyl acetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combination thereof.

The present disclosure is not limited to particular detection systems (e.g., binding pairs or labels). Examples of suitable binding pairs include, but are not limited to, biotin/avidin or streptavidin, colicin E2/Im, *Arabidopsis* Phy-PIF, and Lac repressor (LacI)/Lac operator sequence (LacO).

Examples of suitable detection methods include, but are not limited to, enzymes (e.g., horseradish peroxidase (HRP), alkaline phosphatase (AP) or glucose oxidase), radioactive isotopes, DNA detection (e.g., real-time immunoquantitative PCR (iqPCR) using a DNA probe, fluorogenic reporters (e.g., phycoerythrin), and electrochemiluminescent tags. Substrates for HRP include, but are not limited to, TMB: 3, 3', 5,5'-tetramethyl benzidine (colorimetric), OPD: o-phenylene diamine (colorimetric), ABTS: 2, 2'-azino-bis (3-ethylbenzthiazoline-6-sulfonic acid) (colorimetric), Pierce Supersignal (chemiluminescent), Pierce QuantaBlu (chemifluorescent), and Pierce QuantaRed (chemifluorescent). Substrates for alkaline phosphate include, but are not limited to, pNPP (p-Nitrophenyl Phosphate).

Examples of labels suitable for use in any number of detection methods include, but are not limited to, fluorescent dyes, such as squaric acid-based dyes. In some embodiments, the squaric acid-based dyes are selected from cyclobutenedione derivatives, symmetrical and unsymmetrical squaraines, substituted cephalosporin compounds, fluorinated squaraine compositions, alkylalkoxy squaraines, or squarylium compounds. In another embodiment, the squaric acid-based dyes are selected from a red fluorescent dye and an orange fluorescent dye, such as the red fluorescent dye comprising 1,3-bis(1,3-dihydro-1,3,3-trimethyl-2H-indol-2-ylidene)methyl]-2,4-dihydro xycyclobutenediylium, bis(inner salt) and the orange fluorescent dye comprising 2-(3,5-dimethylpyrrol-2-yl)-4-(3,5-dimethyl-2H-pyrrol-2-ylidene)-3-hydroxy-2-cyclobuten-1-one.

In some embodiments, assay configurations utilize microfluidic systems for assay steps and/or detection methods. In some embodiments, an assay support that comprises microfluidic channels and/or ports is utilized (e.g., for wash, binding, and/or detection steps). In some embodiments, microfluidic devices are made using conventional photolithography and soft lithography, e.g., using a soft polymer (e.g., polydimethylsiloxane (PDMS)), a printed photomask, and a collimated UV light aligner (see, e.g., Quake et al (2000) *Science* 290: 1536-40; Melin et al (2007) *Annu Rev Biophys Biomol Struct* 36:213-31). Methods for fabricating microfluidic devices (including suitable materials, dimensions, design principles, and operation) are provided, for example, in U.S. patent application Ser. Nos. 11/685,654; 11/056,451; 09/826,583; 09/724,784 and 09/605,520, which are incorporated herein by reference in their entireties.

In some embodiments (See e.g., FIG. 7), assays utilize a competition assay comprising known amounts of labeled polyP. In such embodiments, the labeled polyP competes with polyP in the sample for binding to the PE-coated solid support. The amount of labeled (e.g., biotin labeled) polyP is then detected (e.g., using a streptavidin-peroxidase system comprising a chromogenic substrate). Such assays are particularly useful for detecting smaller chains of polyP (e.g., those released from platelets (e.g., 40 to 100 units in length).

In some embodiments (e.g., to improve sensitivity), an ELAST amplification kit (tyramide signal amplification (TSA)) is used to improve sensitivity and enable reduced consumption of detection antibodies in HRP-based ELISA. In some embodiments, fluorescent detection is utilized (e.g., Amplex Ultrared). In some embodiments, detection methods utilize Poly-HRP with Ultra-TMB. In some embodiments, detection methods utilize a chemiluminescence-based method such as SuperSignal ELISA Pico Chemiluminescent Substrate kit.

In some embodiments, standard curves are used to quantify the amount of polyP in a sample. Known quantities of labeled polyP or labeled polyP binding protein are used under assay conditions to generate the standard curves in the absence of sample.

In some embodiments, alternative assays for quantifying inorganic polyphosphate (polyP) in plasma are provided by measuring the concentration-dependent shortening of clot times of plasma that has been spiked with the anticoagulant protein, tissue factor pathway inhibitor (TFPI). Exemplary solution based assays are described in Example 2. In some embodiments, the assays utilize clotting agent (e.g., tissue factor or activated factor X) to induce clotting and a variety of concentrations of TFPI. The levels of inhibition of clotting time is proportional to the level of polyP in the sample. The assays described herein provide a sensitive, functional assay using readily available instrumentation (coagulometers) to quantify polyP in clinical settings.

The assays described herein detect polyP of a variety of lengths (e.g., 20 to 5000 units). In some embodiments, assays are optimized to detect polyP of a length released by platelets (e.g., 60 to 100 units).

The present disclosure is not limited to particular sample types. Examples include, but are not limited to, environmental samples (e.g., water remediation samples comprising microorganisms and water treatment plants) and biological samples (e.g., blood, plasma, serum, cerebrospinal fluid, lavage fluid, or stool).

The assays described herein find use in research, screening (e.g., drug screening), and therapeutic applications. In some embodiments, the assays find use in veterinary applications (e.g., trauma, infection, or cancer detection and screening). In some embodiments, the assays find use in water treatment and remediation applications. In some embodiments, the assays find use in dental applications. In some embodiments, the assays find use in food processing (e.g., processing of meat and fish).

In some embodiments, the assays described herein find use in clinical applications. The presence of polyP in plasma may correlate with increased risk of thrombotic and inflammatory diseases. Circulating polyP may be significant in inflammatory or fibrotic disease conditions such as cancer, sepsis, deep vein thrombosis, clotting disorders, and trauma-induced coagulopathy. Thus, in some embodiments, the level of polyP in a biological sample from a subject is used to diagnose, monitor, study, or determine a treatment course of action in a subject.

EXAMPLES

The following examples are provided in order to demonstrate and further illustrate certain preferred embodiments and aspects of the present disclosure and are not to be construed as limiting the scope thereof.

Example 1

Figure 2:
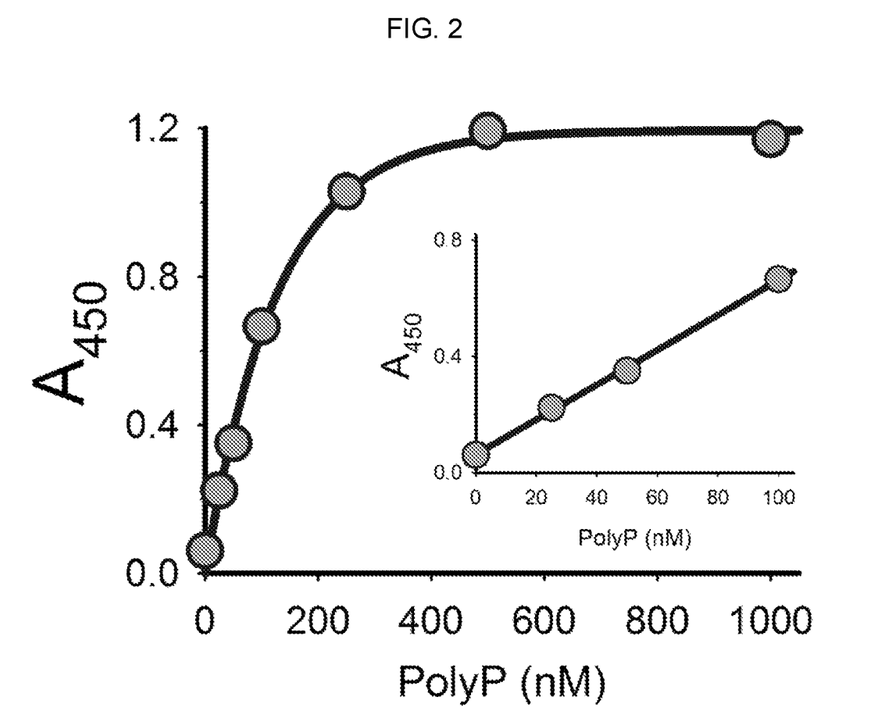
FIG. 2 shows that exemplary assays detects medium and long-chain polyP (>200mer) with sensitivity in the low nM range.
Figure 3:
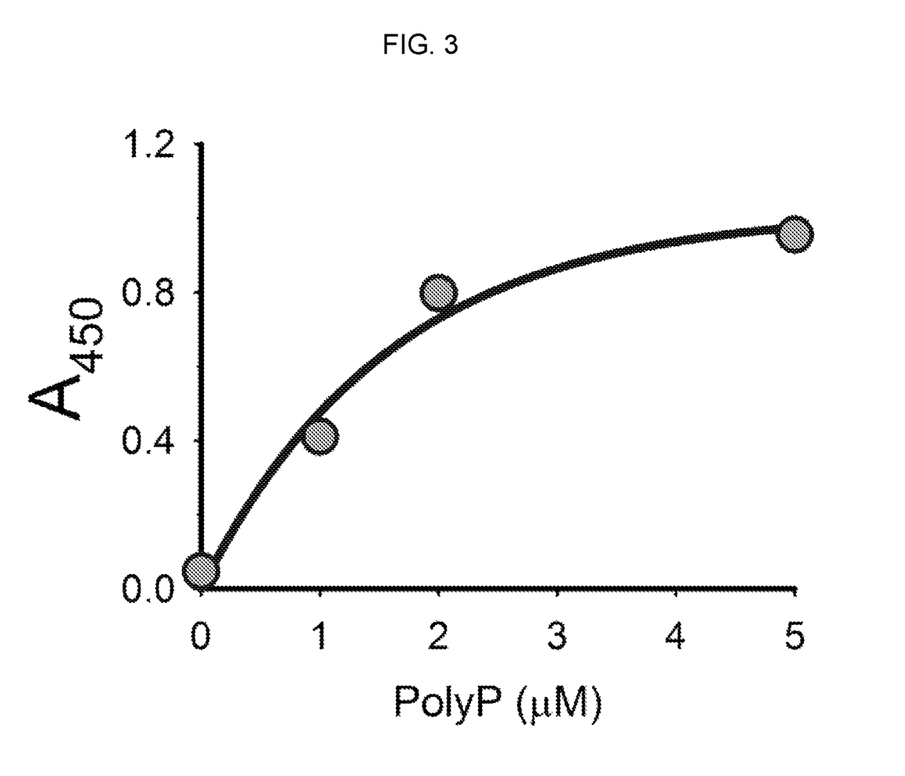
FIG. 3 shows that exemplary assays detects short-chain polyP (≈100mer) with sensitivity in the high nM range.
Figure 7:
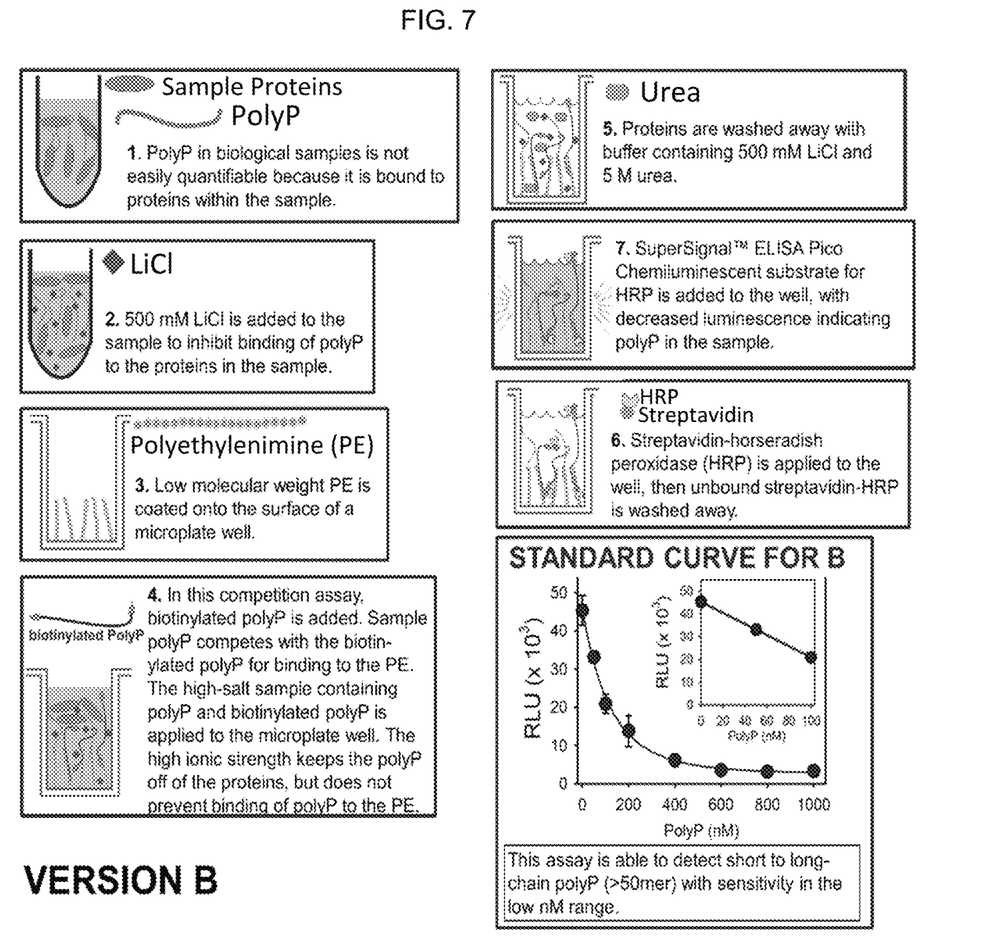
FIG. 7 shows an alternative assay configuration of embodiments of the present disclosure.

Methods: A microplate-based assay that allows the detection and quantification of polyP in the presence of large amounts of polyP-binding proteins and other interfering substances such as are present in plasma was developed (FIG. 1; "version A"). This assay leverages the high binding affinity of polyP for the cationic polymer polyethylenimine (PE). The polyP/PE interaction is resistant to high ionic strength, whereas most proteins will no longer bind polyP under these conditions. In the assay, plasma samples were incubated in a PE-coated microplate well in the presence of EDTA and a high salt concentration. Wells were washed with high concentrations of salt and urea, leaving the captured polyP bound to the PE-coated surface and presumably removing bound plasma proteins from the immobilized polyP. The captured polyP was then detected using a recombinant bacterial polyP-binding protein (*E. coli* biotPPXbd) complexed with streptavidin-peroxidase, after which the bound peroxidase is detected using a chromogenic substrate. A specific assay protocol is provided below:

1. Coat capture agent
   a. Dilute low molecular-weight (LMW) PEI to 2 μg/ml LMW PEI in coating buffer (20 mM Hepes NaOH pH 7.4; 100 mM NaCl; 0.05% NaN$_3$)
   b. Add 100 μL per well
   c. Incubate at room temperature overnight
   d. Wash 3× with 250 μL/well using wash buffer (20 mM Hepes NaOH pH 7.4; 100 mM NaCl; 0.05% Tween 20) and an automatic plate washer
2. Block
   a. Add 200 μL blocking buffer (20 mM Hepes NaOH pH 7.4; 100 mM NaCl; 1% BSA; 0.05% Tween 20; 0.05% NaN$_3$) per well
   b. Incubate 1 hour at room temperature
   c. Wash 3× with 250 μL/well using wash buffer and an automatic plate washer
3. Dilute PolyP700 for standard wells into Sample Diluent (250 mM MES pH 6.0; 2.5 M LiCl; 50 mM EDTA; 0.25% Tween 20)
   a. Final dilutions to 0-500 nM
4. Add Sample Diluent to plasma or serum samples
   a. 4 parts sample+1 part Sample Diluent
5. Add samples and standards to wells
   a. Add 100 μL to well in triplicate
   b. Incubate 1 hour at room temperature
   c. Wash 3× with 250 μL/well using high salt wash buffer (20 mM Hepes NaOH pH 7.4; 5 M urea, 500 mM LiCl; 0.05% Tween 20; 0.05% NaN$_3$) and an automatic plate washer
   d. Wash 3× with 250 μL/well using wash buffer and an automatic plate washer
6. Detection
   a. During PolyP incubation, pre-incubate 2 μg/ml biotPPXbd+1 μg/ml streptavidin-HRP in HRP Diluent (20 mM Hepes pH 7.4, 0.1% BSA, 0.05% Tween20)
   b. After the washing steps, add 100 μL to each well
   c. Incubate 1 hour at room temperature
   d. Wash 3× with 250 μL/well using wash buffer and an automatic plate washer
   e. Prepare TMB substrate according to manufacturer's instructions
   f. Add 100 μL substrate to each well
   g. Incubate 10-15 minutes at room temperature
   h. Stop reaction by adding 100 μL 2M H$_2$SO$_4$ to each well
   i. Read A$_{450}$ In an alternative assay configuration (FIG. 7; "version B"), a known quantity of biotinylated polyP is added to plasma samples, which were then incubated in PEI-coated microplate wells in the presence of EDTA and a high salt concentration. Wells were then washed with high concentrations of salt and urea. Under these conditions, the polyP-protein interactions in the sample are disrupted, leaving the captured polyP bound to the PEI-coated surface and removing plasma proteins from the immobilized polyP. The biotinylated polyP and the sample polyP compete for the limited PEI binding sites on the well surface. The more sample polyP that is present, the less biotinylated polyP will bind. Any unbound polyP and the plasma proteins was then washed away using a high salt/urea wash buffer. Streptavidin-horse radish peroxidase (HRP) was then applied to the well. Any unbound streptavidin-HRP was then washed away. The bound biotinylated polyP was then detected using a substrate for the HRP. This version is optimized for detection of short chain polyP (e.g., 60 to 100 units) released from platelets. A specific assay protocol is provided below:

1. Coat capture agent to 96 well plate
   a. Dilute LMW PEI to 0.5 μg/ml LMW PEI in coating buffer (20 mM Hepes NaOH pH 7.4; 100 mM NaCl; 0.05% NaN$_3$)
   b. Add 100 μL per well
   c. Incubate at room temperature overnight
   d. Wash 3× with 250 μL/well using wash buffer (20 mM Hepes NaOH pH 7.4; 100 mM NaCl; 0.05% Tween 20) and an automatic plate washer
2. Block
   a. Add 200 μL blocking buffer (20 mM Hepes NaOH pH 7.4; 100 mM NaCl; 1% BSA; 0.05% Tween 20; 0.05% NaN$_3$) per well
   b. Incubate 1 hour at room temperature
   c. Wash 3× with 250 μL/well using wash buffer and an automatic plate washer
3. Dilute biotPolyP to 1 μM into Sample Diluent
4. Dilute standard PolyP for standard wells into Sample Diluent
   a. Final dilutions to 0-1000 nM (2×, final well concentrations 0-500 nM)
5. Add Sample Diluent to plasma or serum samples
   a. 4 parts sample+1 part Sample Diluent (250 mM MES pH 6.0; 2.5 M LiCl; 50 mM EDTA; 0.25% Tween 20)
6. Mix biotPolyP and samples or standards 1:1
   a. 160 μL biotPolyP+160 μL sample or standard prepared as above
7. Add samples and standards with biotPolyP to wells
   a. Add 100 μL to well in triplicate
   b. Incubate 1 hour at room temperature
   c. Wash 3× with 250 μL/well using high salt wash buffer (20 mM Hepes NaOH pH 7.4; 5 M urea, 500 mM LiCl; 0.05% Tween 20; 0.05% NaN$_3$) and an automatic plate washer
   d. Wash 3× with 250 μL/well using wash buffer and an automatic plate washer 8. Detection
   a. Dilute streptavidin-HRP to 1 µg/ml in HRP Diluent
   b. Add 100 µL to each well
   c. Incubate 1 hour at room temperature
   d. Wash 3× with 250 µL/well using wash buffer and an automatic plate washer
   e. Prepare substrate according to manufacturer's instructions
   f. Add 100 µL substrate to each well
   g. Mix for 1 min
   Read Luminescence Results: Results are shown in FIGS. 2-3 and 7. FIG. 2 shows that the version A assay detects medium and long-chain polyP (>200mer) with sensitivity in the low nM range. FIG. 3 shows that the version A assay detects short-chain polyP (=100mer) with sensitivity in the high nM range. FIG. 7 shows that the version B assay detects short chain polyP with sensitivity in the low nM range.

During the course of development of embodiments of the present disclosure, a variety of capture agents were assayed. PPXbd was assayed as both a capture agent and a detection agent (analogous to a sandwich ELISA), which was not successful because of dimerization of the PPXbd. Histones (mixed from calf thymus), H3.1, and H3/H4 tetramer were assayed. Background signal was an issue, and the detection agent (PPXbd) bound non-specifically to the histones. High molecular weight PEI (Mn 60,000 (where Mn is the number average molecular weight)), linear (Mn 2500), branched PEI (Mw 600), end-capped PEI (Mn 600), sheared short-chain PEI were assayed. PAMAM Dendrimer generations 0, 3, 6, 7 were assayed. However, some of these polymers such as the lower-generation dendrimers could not tolerate the high salt concentration necessary for stripping polyP off of the proteins.

In summary, the assay can detect long-chain polyP (present in bacteria and also released by certain mammalian cell types) in plasma with a linear working range of 10-100 nM (measured in terms of phosphate monomer). It can detect shorter-chain polyP (of the size range secreted from activated platelets and mast cells) with a working range of 50-500 nM.

In order to further explore the role of polyP in various pro-thrombotic and proinflammatory conditions, the assay can be used to evaluate patient samples for the presence of polyP.

Example 2

Figure 4:
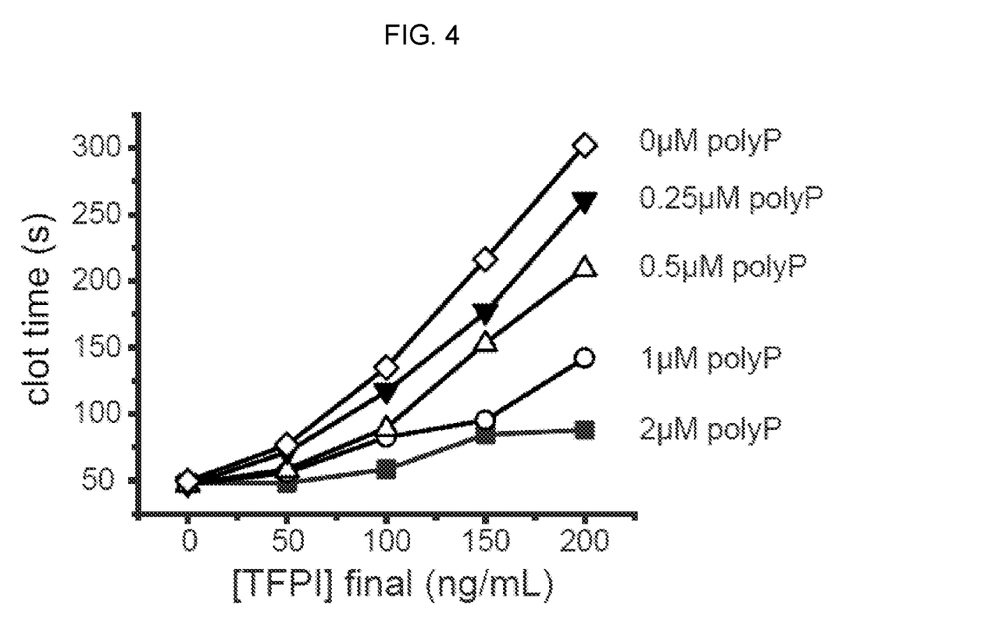
FIG. 4 shows dose-dependent effect of TFPI and polyP on clot times.

In this assay, clotting of a human plasma sample is triggered by a diluted thromboplastin reagent (whose active ingredient is tissue factor, or TF), such that the clotting time of normal plasma is approximately 50 seconds. Increasing concentrations of TFPI are then added to the plasma, such that the clotting times are prolonged by this anticoagulant protein. When polyP is added to such clotting assays, it essentially neutralizes the anticoagulant activity of TFPI in a manner that is dependent on the polyP concentration (FIG. 4). The inability of TFPI to exert its anticoagulant effect in the presence of polyP is referred to as "TFPI resistance". Plasma samples exhibiting TFPI resistance are therefore suspected of containing polyP or a related substance.

General clotting protocol: TF (5 ng/mL initial) and phospholipid vesicles (150 µM, 80:20 phosphatidylcholine:phosphatidylserine) are added to HBA (20 mM Hepes pH 7.4, 0.1% bovine serum albumin, 0.02% $NaN_3$) to make clotting reagent. To a portion of this reagent, TFPI is added at 3× the final concentration. Typically, citrated plasma is thawed and all materials are warmed to 37° C. In a pre-warmed cuvette, 50 µL of clotting reagent (+/−TFPI), 50 µL of plasma (+/−polyP) and 25 µL of water (+/−inhibitor) are incubated for 50 s, then clotting is initiated by the addition of 25 µL of 50 mM $CaCl_2$. PolyP is included in either the plasma portion (simulating a clinical sample) or the water portion of the experiment. Regardless, the concentrations of polyP are here represented as the concentration of polyP present in the plasma portion of the clot, as if the polyP present were coming from a patient plasma sample.

Figure 5:
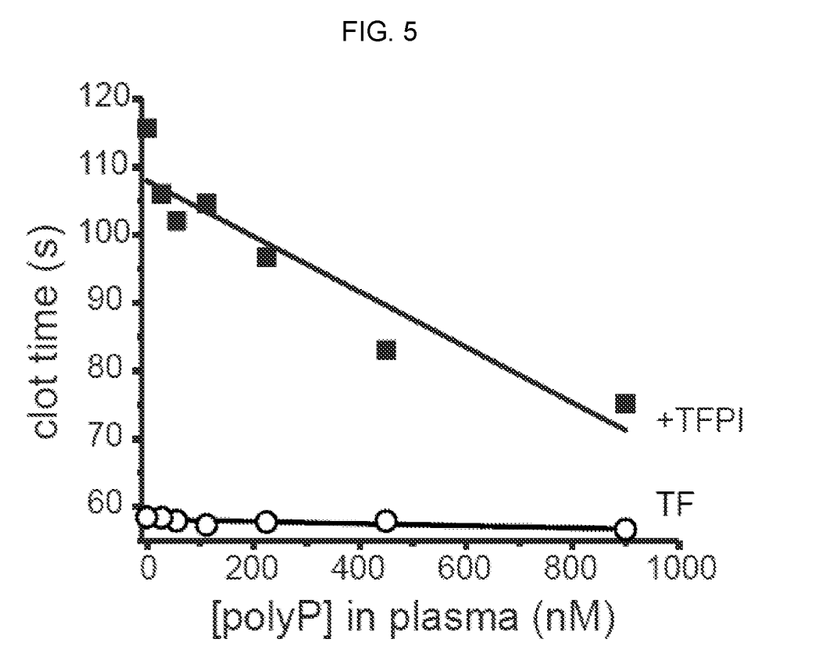
FIG. 5 shows a standard curve correlating concentration of polyP to TFPI clot time.

To perform the clinical assay, standards were created by spiking different concentrations of polyP into citrated plasma and incubating with clotting reagent with fixed concentrations of both TF (1.7 ng/mL final concentration in the clotting mixture) and TFPI (45 ng/mL final concentration in the clotting mixture). The clotting times of these samples were then used to make a standard curve (FIG. 5) correlating the polyP concentration to the clot time. The presence of polyP creates TFPI resistance, reducing clot times. The linear range of such assays is typically from about 10 nM to 900 nM polyP (in terms of phosphate monomer concentration). A patient sample is then analyzed using the same conditions (diluting the sample if needed), using clot times to calculate an effective polyP concentration. A typical standard curve is given in FIG. 5.

Figure 6:
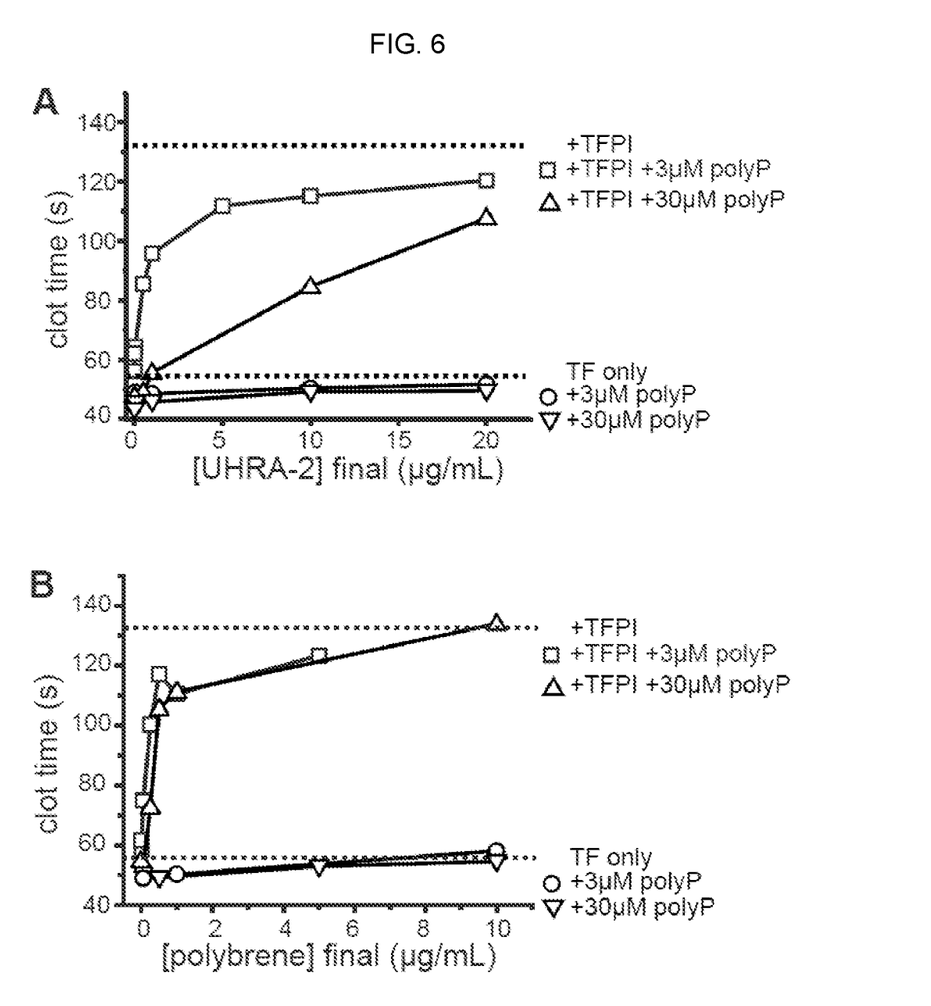
FIG. 6 shows dose response of the ability of polyP inhibitors to reverse TFPI resistance.

In order to confirm that polyP is the substance in a given plasma sample that is responsible for the TFPI resistance, known polyP inhibitors were used to reverse this effect. Neither UHRA-2 nor polybrene (at the concentrations used here) affected TF-initiated clot times. The final plasma clotting mixtures contained either no added TFPI or 150 ng/mL added TFPI, as indicated (FIG. 6). PolyP was added to some plasma samples at 3 or 30 µM, as indicated. Varying concentrations of either UHRA-2 (Panel A) or polybrene (Panel B) were then also added to the clotting reactions. In samples without added TFPI, the presence of UHRA-2 or polybrene had little or no effect on the clotting time. However, these polyP inhibitors clearly reversed the ability of polyP to cause TFPI resistance. However, in the presence of polyP, adding either UHRA-2 or polybrene returned clot times to near TFPI levels as seen in the absence of polyP (FIG. 6). This confirms that the shortened clot times seen in the FIGS. 4 and 5 were due to TFPI resistance from polyP, and not to some other pro-coagulant activator that interferes with TFPI via a different mechanism. In a clinical assay, these inhibitors may be used at a fixed concentration to abrogate the polyP effect across the linear range of the assay, thereby confirming that the observed TFPI resistance was due to polyP.

Figure 8:
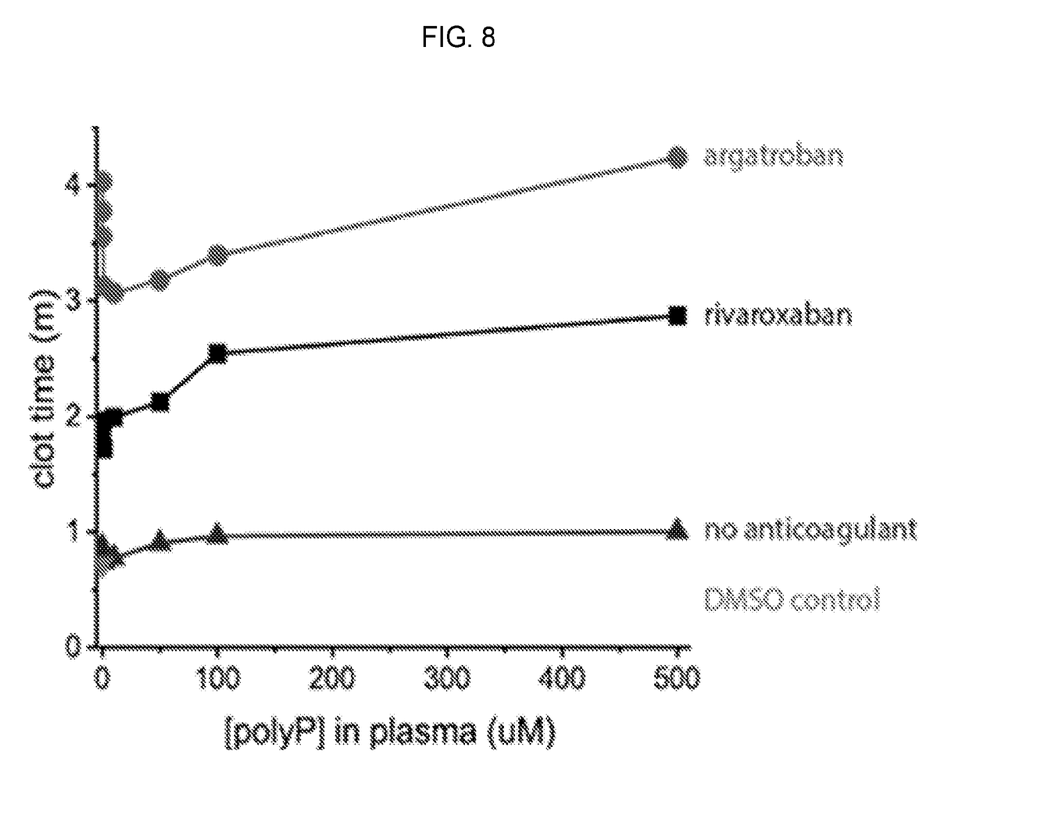
FIG. 8 shows that polyP has limited ability to alter the clotting times of samples treated with rivaroxaban or argatroban.

Further experiments demonstrated that other anticoagulants (as a substitute for TFPI) do not have the same sensitivity to polyP. PolyP spiked into plasma containing these anticoagulants did not return clot times back to those without these drugs with the sensitivity necessary for a polyP-detection assay (FIG. 8).

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of detecting polyphosphate in a sample, comprising:
   a) contacting a sample comprising polyphosphate with an agent that inhibits binding of said polyphosphate to proteins in said sample;
   b) contacting said sample with a solid support coated in a polymer under conditions such that said polyphosphate binds to said polymer;
   c) washing said solid support to remove proteins in said sample;
   d) contacting said solid support with a polyphosphate binding protein under conditions such that said polyphosphate binding protein binds to polyphosphate; and
   e) quantifying the level of polyphosphate binding protein bound to said polyphosphate.

2. A method of detecting polyphosphate in a sample, comprising:
   a) contacting a sample comprising polyphosphate with an agent that inhibits binding of said polyphosphate to proteins in said sample and a known amount of labeled polyphosphate;
   b) contacting said sample with a solid support coated in a polymer under conditions such that said polyphosphate binds to said polymer;
   c) washing said solid support to remove proteins in said sample; and
   d) quantifying the level of labeled polyphosphate.

3. The method of claim 1, wherein said polymer is polyethylenimine.

4. The method of claim 1, wherein said agent is a salt.

5. The method of claim 4, wherein said salt is LiCl.

6. The method of claim 1, wherein said solid support comprises a sample well.

7. The method of claim 1, wherein said polyphosphate binding protein is *E. coli* polyP-binding protein (PPXbd).

8. The method of claim 1, wherein said polyphosphate binding protein is labeled.

9. The method of claim 8, wherein said label is biotin.

10. The method of claim 1, wherein said labeled polyphosphate is labeled with biotin.

11. The method of claim 1, wherein said quantifying comprises contacting said sample with streptavidin-peroxidase and a substrate for said peroxidase.

12. The method claim 1, wherein said washing said sample comprises washing with a buffer comprising urea and a salt.

13. The method of claim 12, wherein said quantifying comprising comparing the amount of substrate to a standard curve.

14. The method of claim 1, wherein said sample is a biological sample or an environmental sample.

15. The method of claim 14, wherein said environmental sample is a water sample.

16. The method of claim 14, wherein said biological sample is selected from the group consisting of blood, plasma, serum, cerebrospinal fluid, lavage fluid, and stool.

17. The method of claim 1, wherein said polyphosphate is 20 to 5000 units in length.

18. The method of claim 16, wherein the sample is from a human subject.

19. The method of claim 18, wherein said subject is diagnosed with or suspected of having a disease or condition selected from the group consisting of deep vein thrombosis, sepsis, trauma, cancer, a clotting disorder, an inflammatory disease, and a fibrotic disease.

* * * * *

UNITED STATES PATENT AND TRADEMARK OFFICE
CERTIFICATE OF CORRECTION

| | |
|---|---|
| PATENT NO. | : 11,519,917 B2 |
| APPLICATION NO. | : 16/604269 |
| DATED | : December 6, 2022 |
| INVENTOR(S) | : James H. Morrissey et al. |

It is certified that error appears in the above-identified patent and that said Letters Patent is hereby corrected as shown below:

In the Claims

Claim 1, Column 13, Line 6 reads:
"proteins in said sample;"
Whereas it should read:
--proteins in said sample and a known amount of labeled polyphosphate;--

Signed and Sealed this
Fourteenth Day of March, 2023

Katherine Kelly Vidal
*Director of the United States Patent and Trademark Office*